US00PP09319P

United States Patent [19]

Bennett,

[11] Patent Number: Plant 9,319

[45] Date of Patent: Oct. 10, 1995

[54] MINIATURE ROSE PLANT NAMED 'TINY PETALS'

[76] Inventor: Cecilia L. D. Bennett, deceased, late of Chula Vista; by Susan M. O'Brien, administrator, 489 Minot Ave., Chula Vista, both of Calif. 91910

[21] Appl. No.: 177,601

[22] Filed: Jan. 3, 1994

[51] Int. Cl.[6] ..... A01H 5/00

[52] U.S. Cl. ..... Plt./7.1

[58] Field of Search ..... Plt./7.1, 10

*Primary Examiner*—Howard J. Locker

[57] ABSTRACT

The subject of the present disclosure is a new and distinct variety of miniature rose plant, named 'Tiny Petals' which is characterized by buds and blooms in shades of scarlet to coral-red. Blooms of this rose are usually borne one to a stem with hybrid tea form and in sprays of 3 to 5 or more. The bush is vigorous, well-branched and produces moderate to heavy blooms.

1 Drawing Sheet

The present invention relates to a new and distinct variety of a hardy, dwarf, bush plant of the miniature class; the variety being primarily characterized as a red blend.

The variety is further characterized by:

Long stemmed blooms of hybrid tea-type form, borne usually one to a stem and in compact sprays of 3 to 5 or more. The blooms are held very erect and well above the foliage.

The plant ranges in height from 18 to 24 inches (45 to 60 cm). The canes are sturdy and erect with moderate branching and medium to heavy foliage covering. The plant is a heavy bloomer that does well either in the greenhouse or outdoors.

The plant has good growth habits, is well-shaped and attractive, bearing numerous leaflets of average size. Asexual reproduction of the new variety by cuttings derived from the plant stem, as performed at Chula Vista, Calif., shows that the foregoing and other characteristics and distinctions come true to form and are established and transmitted through succeeding propagations.

The seed parent was San Antonio (U.S. Plant Pat. No. 2,844), and the pollen parent was Jean Kenneally (U.S. Plant Pat. No. 5,637). It differs from its seed parent in the following ways. It is a miniature rose of the red blend class and San Antonio is a grandiflora in the orange-red class. It differs from its pollen parent in the following ways. It produces blooms in shades of red with a pale yellow reverse, and Jean Kenneally produces blooms in apricot.

The single color photographic view shows, in plain view, a bouquet of 'Tiny Petals' in various stages of maturity from bud stage to nearly open bloom stage.

The descriptive matter which follows pertains to roses grown and color values observed in plants and newly opened blooms in the months of March through November of 1993. The plants were grown outdoors in Chula Vista, Calif., and are believed to be accurate standards for this cultivar in similar conditions of soil and climate elsewhere.

Referring now specifically to the new and distinct variety of miniature rose plant named 'Tiny Petals', the following is a detailed desription thereof in outline; all major color plate identifications being by reference to the British Colour Council Horticultural Chart, except where common terms of color definition are employed.

Type: Hardy, dwarf, bushy, greenhouse or outdoor, exhibition or garden decorative potted plant.

Class: Miniature.

Variety name: Tiny Petals.

Flowers borne: Usually one to a stem, but occasionally in sprays of 3 to 5 or more on erect stems with foliage well below the blooms.

Quantity of bloom: Heavy both outdoors or greenhouse grown.

Bud:

*Peduncle.*—Average length (30 to 50 mm); average diameter and sturdy; ranging from near Scheeles Green (860/3 to 860/1 page 176) with occasional tinting of bronze.

*Hairs.*—Extremely small and sparse with a reddish color; located over the surface of the peduncle and calyx tube.

*Calyx.*—Color range same as peduncle.

*Opening.*—Opens well in all weather.

Bloom:

*Size when fully open.*—Average for a miniature variety (40 to 50 mm).

*Petalage.*—Full — 25 to 35 petals, arranged regularly, plus 5 to 10 petaloids.

*Form.*—Urn-shaped to ovoid as the bloom opens. The petals remain somewhat cupped with the apex and/or margins reflexed outward, becoming at maturity more loosely cupped.

Petals: Fairly thick with good substance; both the upper and under surfaces of all petals have a matte finish.

*Shape.*—Outer petals are of a broad obovate form. The intermediate petals are very much like the outer petals only narrower. The inner petals are a broad lanceolate form; and the petaloids are also lanceolate with some occasional irregularities.

Color: Newly opened flowers from plants grown outdoors (March through November of 1993), Chula Vista, Calif.

*All petals.*—Upper surfaces — Ranging from near Geranium Lake (20/2 to 20 page 20) to near Scarlet (19/2 to 19 page 19). Under surfaces — Ranging from near Egyptian Buff (407/3 to 407/1 Page 122) to Maize Yellow (607/3 to 607/1 Page 69). *General Color Effect:* Newly opened flowers — Medium red blooms with a reverse of pale yellow to cream. Three days open — Slight fading of petals. Three to five days open — Continued fading of all petals to softer tones of red with cream reverse. *Flower Longevity:* (March through November 1993) Plant in pot 5 to 7 days from bud with sepals reflexed to fully open bloom. Holding at fully opened for 5 to 7 days longer. Cut blooms at living room temperature 10 to 14 days or longer.

Reproductive Organs:

*Stamens.*—A generous amount arranged uniformly around the pistil.

*Filaments.*—Varying in length with shorter filaments more proximal to the pistil; pale yellow in color with anthers of golden yellow.

*Pollen.*—Abundant.

*Pistil.*—Short, spreading and abundant; pale yellow.

*Ovaries.*—All encased in calyx.

*Hips.*—Some.

*Seeds.*—3 to 5 or more in each hip.

Foliage:

*Sepals.*—Permanent; simple and glabrous; spear-shaped; open as the bloom opens, recurving against the peduncle, when the bloom is fully opened. Occasional foliaceous appendages attractively supplement sepal terminals; these are of varying lengths.

*Leaves.*—5 to 7 leaflets on average; medium size for a miniature rose plant.

*Leaflets.*—Broad ovate-shaped.

*Margins.*—Very serrated with tinting of bronze, especially noticeable on the newer foliage.

Color.—Ranging from near Spinach Green (0960/3 to 0960 page 187) to near Scheeles Green (860/1 to 860 page 175) with occasional bronzing of the margins, especially on the newer foliage. Upper surfaces have a semi-glossy finish, and the under surfaces have a matte finish of a slightly lighter shade than the upper surfaces.

*Rachis.*—Medium strength; upper surface is grooved with very small hairs over the length of it. Under surface has few if any hairs but does contain 2 to 5 small prickles.

*Stipules.*—Varying in length from small to medium; average width; tapering auricles angled outward at about 45 degrees.

Growth:

*Habit.*—Dwarf, bush; above average for a miniature rose plant.

*Rate and character.*—Vigorous and well-branched.

*Canes.*—Medium diameter; sturdy; held erect.

*Main stems.*—Color range same as foliage.

*Thorns.*—Averaging less than 5 to 10 per 10 cm on the main stems and branches. Reddish in color; average size; slender and hooked slightly downward.

*Branches.*—Coloration ranges the same as does that of the foliage.

The miniature rose plant and its flowers as herein described may vary in slight detail due to climate, soil and cultural conditions under which the variety may be grown; the present description being of the variety as grown in Chula Vista, Calif.

No information related to insect, disease or frost tolerance is available due to the controlled growing conditions under which our plants are produced and maintain, which includes regular application of fungicides and pesticides on all plants and the immediate elimination of any inferior seedlings which demonstrate a tendency to develop diseases or other unpleasant habits. As to frost tolerance, all of our plants are grown in Chula Vista, Calif. which is located in a moderate temperature zone that would rarely experience frost or freezing temperatures. For the above mentioned reasons, the specifications have not been expanded further.

The following is claimed:

1. A new and distinct variety of miniature rose plant, named 'Tiny Petals'; the plant characterized as hardy, dwarf, by its vigorous growth, well-branched and attractive appearance, substantially as illustrated and described; and characterized further by its hybrid tea form blooms, ranging from near Scarlet to near Geranium Lake with a reverse of near Egyptian Buff to near Maize Yellow, the blooms being abundant on the bush and usually borne one to a stem but occasionally in sprays of 3 to 5 more.

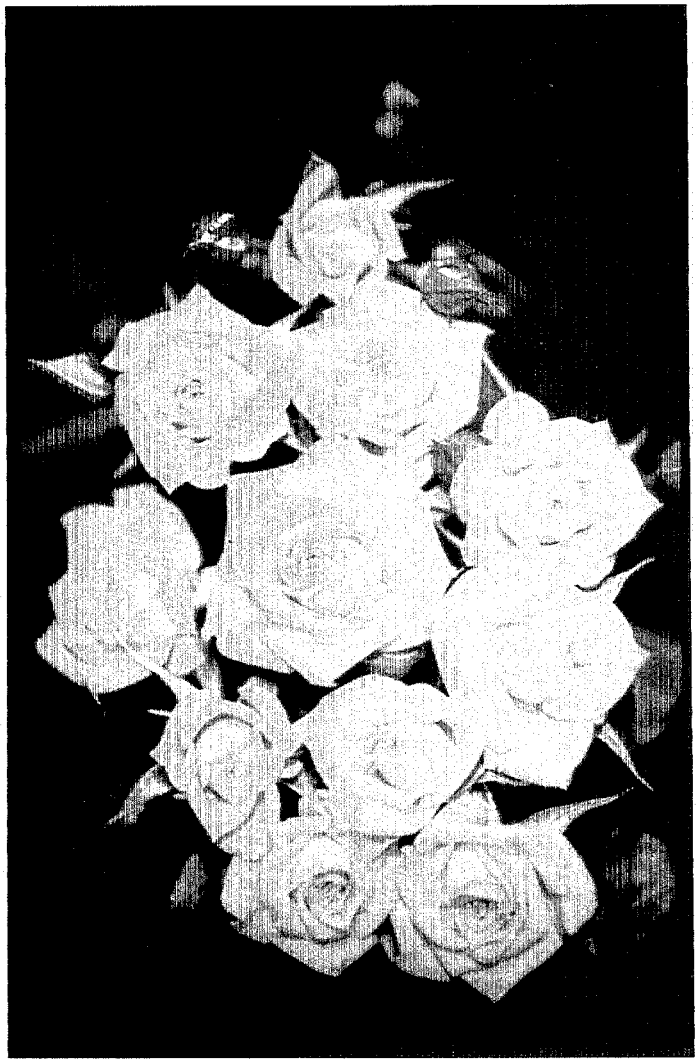

* * * * *